(12) United States Patent
Matsuba et al.

(10) Patent No.: US 8,750,584 B2
(45) Date of Patent: Jun. 10, 2014

(54) MEDICAL IMAGE DISPLAY PROCESSING METHOD, DEVICE, AND PROGRAM

(75) Inventors: Seiji Matsuba, Tokyo (JP); Tetsutaro Ono, Tokyo (JP); Tomoaki Goto, Tokyo (JP); Kunihiko Kasahara, Tokyo (JP); Hiroshi Matsuda, Iruma-gun (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 276 days.

(21) Appl. No.: 13/497,447

(22) PCT Filed: Sep. 17, 2010

(86) PCT No.: PCT/JP2010/066236
§ 371 (c)(1),
(2), (4) Date: Mar. 21, 2012

(87) PCT Pub. No.: WO2011/037093
PCT Pub. Date: Mar. 31, 2011

(65) Prior Publication Data
US 2012/0195485 A1 Aug. 2, 2012

(30) Foreign Application Priority Data
Sep. 25, 2009 (JP) .................................. 2009-221391

(51) Int. Cl.
*G06K 9/00* (2006.01)
*A61B 5/05* (2006.01)
*A61B 5/04* (2006.01)
(52) U.S. Cl.
USPC ............................ 382/128; 600/410; 600/544
(58) Field of Classification Search
None
See application file for complete search history.

(56) References Cited

U.S. PATENT DOCUMENTS

| 7,627,370 | B2 * | 12/2009 | Marks | 600/544 |
|---|---|---|---|---|
| 8,626,264 | B1 * | 1/2014 | Beran | 600/407 |
| 2010/0174117 | A1 * | 7/2010 | Heidemann et al. | 564/485 |
| 2010/0204563 | A1 * | 8/2010 | Stodilka et al. | 600/411 |

FOREIGN PATENT DOCUMENTS

| JP | A-2001-112733 | 4/2001 |
|---|---|---|
| JP | A-2003-199715 | 7/2003 |
| JP | A-2003-339670 | 12/2003 |
| JP | A-2005-237441 | 9/2005 |

OTHER PUBLICATIONS

Wang et al., "Reduced susceptibility effects in perfusion fMRI with single-shot spin-echo EPI acquisitions at 1.5 Tesla", Magnetic Resonance Imaging 22 (2004) 1-7, 2004.*

(Continued)

*Primary Examiner* — Anand Bhatnagar
*Assistant Examiner* — Soo Park
(74) *Attorney, Agent, or Firm* — Oliff PLC

(57) ABSTRACT

When brain images are inputted through MRI (Magnetic Resonance Imaging) and subjected to image processing to assist the diagnosis of brain diseases, functional and morphological images in an ASL coordinate system are inputted from the head of a subject by an ASL (Arterial Spin Labeling) imaging method using an MRI device. The inputted functional images are subjected to mask processing to extract only the region of cerebral parenchyma, and functional images of only the extracted region of the cerebral parenchyma are thereby produced and displayed to be overlaid on the morphological images. In this manner, a functional image such as a perfusion weighted image of only the region of the cerebral parenchyma can be extracted and displayed overlaid on a morphological image.

15 Claims, 14 Drawing Sheets

(56) References Cited

OTHER PUBLICATIONS

Bartsch et al., "Diagnostic functional MRI: illustrated clinical applications and decision-making", Journal of Magnetic Resonance Imaging 23:921-932, 2006.*

Fernandez-Seara et al., "Continuous Arterial Spin Labeling perfusion measurements using single shot 3D GRASE at 3T", Magnetic Resonance in Medicine 54:1241-1247, 2005.*

Tjandra et al. "Quantitative assessment of the reproducibility of functional activation measured with BOLD and MR perfusion imaging: implications for clinical trial design", NeuroImage 27 (2005) 393-401, 2005.*

Hiroshi Matsuda, "MRI ni yoru Ninchisho Shindan no Genjo to Tenbo," *Shin Iryo*, 2009, vol. 36, No. 6, pp. 53-56 (with English-language summary).

Wen-Ming Lim at al., "Quipss II With Thin-Slice TI$_1$ Periodic Saturation: A Method for Improving Accuracy of Quantitative Perfusion Imaging Using Pulsed Arterial Spin Labeling," *Magnetic Resonance in Medicine*, 1999, vol. 41, pp. 1246-1254.

K.J. Friston et al., "Spatial Registration and Normalization of Images," *Human Brain Mapping*, 1995, vol. 2, pp. 165-189.

J. Ashburner et al., "Incorporating Prior Knowledge into Image Registration," *NeuroImage*, 1997, vol. 6, pp. 344-352.

J. Ashburner at al., "Nonlinear Spatial Normalization Using Basis Functions," *Human Brain Mapping*, 1999, vol. 7, pp. 254-266.

Nov. 16, 2010 International Search Report issued in International Patent Application No. PCT/JP2010/066236 (with translation).

\* cited by examiner

Fig. 4
(A)
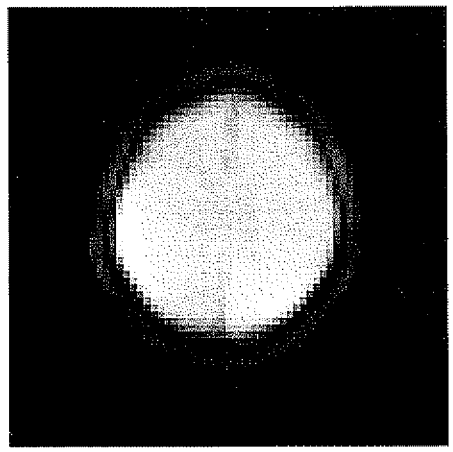
EXAMPLE OF ASL-EPI IMAGE
(LOW RESOLUTION)
(B)
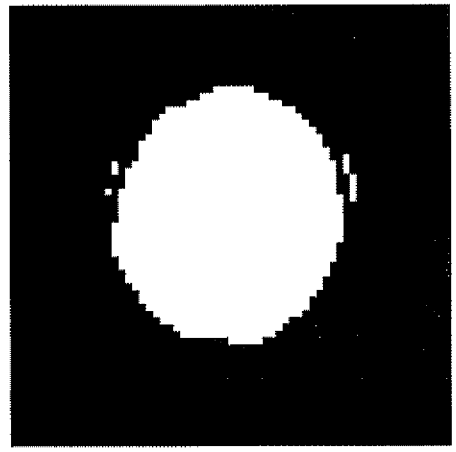
MASK IMAGE OBTAINED BY
BINARIZATION OF ASL-EPI IMAGE Fig. 5
(A)
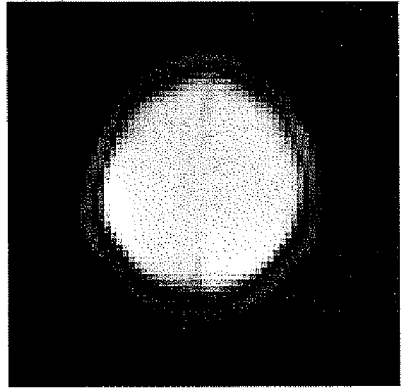
(1) EXAMPLE OF ASL-EPI IMAGE
(LOW RESOLUTION)
(B)
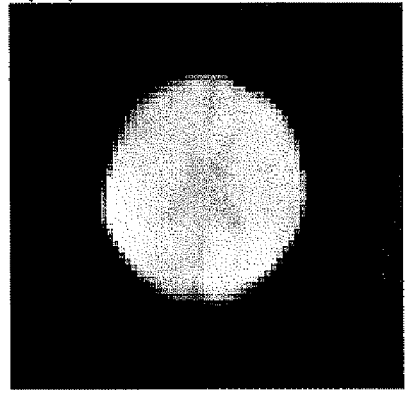
(2) IMAGE OBTAINED BY SEPARATING GRAY MATTER, WHITE MATTER, AND CEREBROSPINAL FLUID FROM EACH OTHER AND COMBINING REGION OF GRAY MATTER AND REGION OF WHITE MATTER
(C)
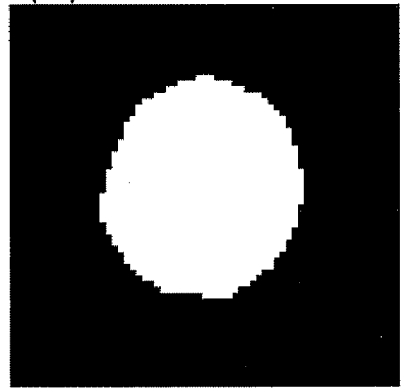
(3) MASK IMAGE OBTAINED BY BINARIZING ASL-EPI IMAGE IN (2) AND THEN SUBJECTING IT TO FILLING PROCESSING

CONCEPTUAL DIAGRAM OF DEFORMATION FIELD

○ : COORDINATE POSITIONS OF ORIGINAL IMAGE
● : COORDINATE POSITIONS AFTER TRANSFORMATION
ARROWS : TRANSFORMATION FIELD

Fig. 11
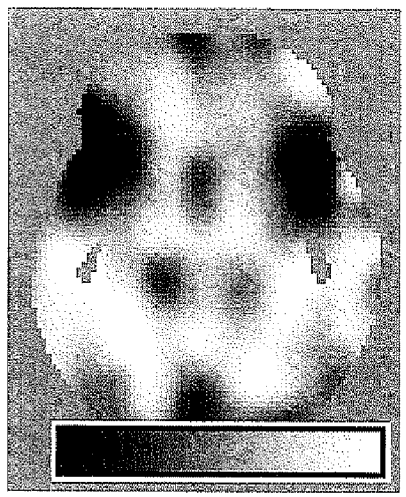
(A)
PERFUSION WEIGHTED IMAGE
Z SCORE MAP
(STANDARD BRAIN)
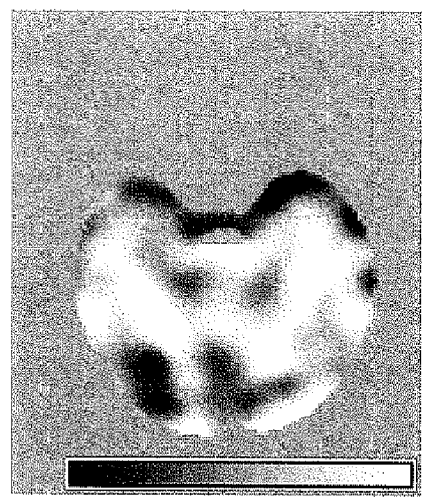
(B)
PERFUSION WEIGHTED IMAGE
Z SCORE MAP
(SUBJECT BRAIN)

Fig. 12
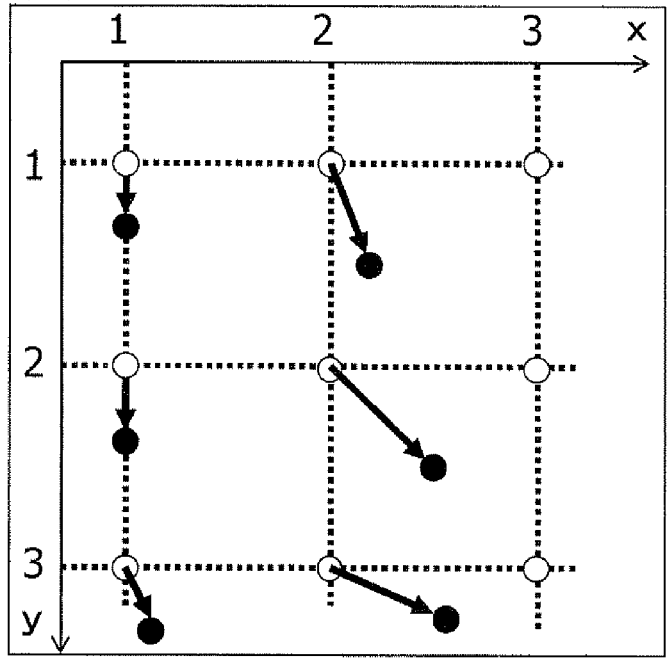
TRANSFORMATION OF COORDINATES USING DEFORMATION FIELD f
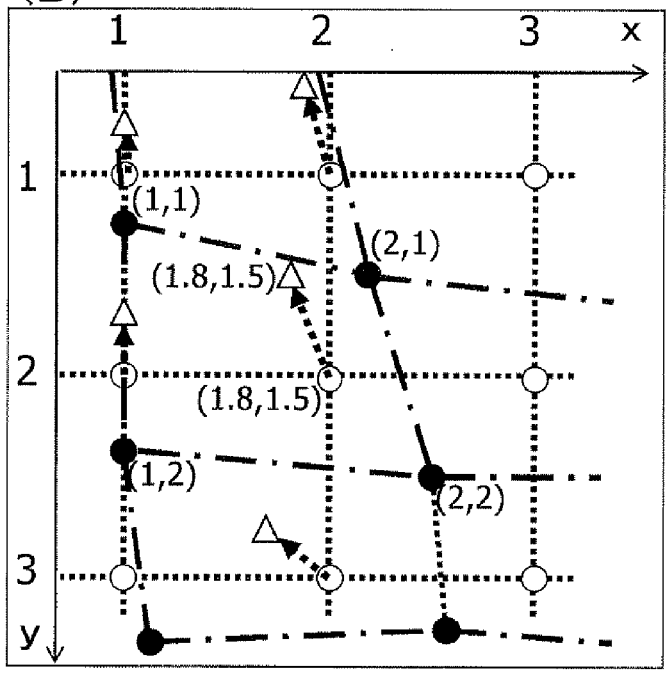
TRANSFORMATION OF COORDINATES USING DEFORMATION FIELD g

MEDICAL IMAGE DISPLAY PROCESSING METHOD, DEVICE, AND PROGRAM

TECHNICAL FIELD

The present invention relates to medical image display processing methods, devices, and programs and particularly to a medical image display processing method, device, and program suitably used when brain images inputted through MRI (Magnetic Resonance Imaging) are subjected to image processing to assist the diagnosis of brain diseases.

BACKGROUND ART

With the advent of an aging society, the number of patients with dementia is increasing year by year. There are various types of dementia, and it is important to determine the type of dementia by diagnosis so that the disease is treated appropriately according to the determined type.

To respond to such a demand, an ASL imaging method (hereinafter may be simply referred to as an ASL method) based on ASL (Arterial Spin Labeling) is recently being used as a novel perfusion weighted imaging technique using MRI.

PWI (Perfusion Weighted Imaging) (also referred to as perfusion imaging) is a technique for imaging perfusion, which is the flow of blood through capillary vessels in tissues (see, for example, Patent Literature 1). The state of perfusion can be known by marking blood on the upstream (arterial) side of the tissues and observing the passage of the blood flowing through the tissues.

In a general conventional method, a contrast medium containing a radioactive isotope serving as a tracer is injected into an artery, and the injected radioactive isotope is observed. However, this method has an invasion problem.

The ASL method is characterized in that perfusion weighted images can be noninvasively obtained without any contrast medium.

The principle of the ASL method is as follows. A carotid artery is irradiated with inversion pulses to spin-label protons in blood flowing through the carotid artery, and images of the head are taken after a predetermined time, i.e., after the brain is perfused with the blood. These images are used as labeled images. Similarly, images are taken without irradiation with inversion pulses and are used as non-labeled images.

The above procedure is repeated to obtain a group of labeled images and a group of non-labeled images. PWIs quantitatively showing the distribution of cerebral blood flow can be obtained by the difference between the group of labeled images and the group of non-labeled images.

In addition, absolute CBFs (Cerebral Blood Flows) can be obtained from the PWIs. More specifically, the absolute CBFs are determined by substitution of the time of passage of the labeled blood, a blood-brain partition coefficient, the longitudinal relaxation time of the blood, etc. (see Non Patent Literature 1).

Generally, labeled images and non-labeled images are taken using a fast imaging sequence such as EPI (Echo Planar Imaging). Such a fast imaging sequence allows fast imaging, but the resolution of the images is low. However, when there is a need to take additional high resolution MRI images using a conventional imaging method, an imaging sequence that can provide additional high resolution images may be performed subsequent to the imaging procedure using the ASL method with the subject being secured.

The above-described and other features of the ASL method are summarized as follows:—Perfusion weighted images can be noninvasively obtained without any contrast medium. Morphological images (low-resolution images), together with functional images including PWIs and CBFs, are obtained by the ASL method, and the positions in the obtained images completely match each other. Morphological images (high-resolution images) can be taken using a conventional method subsequent to the imaging by the ASL method, and the positions in the morphological images substantially match the positions in the PWIs and CBFs.

As described above, PWIs and CBFs are very useful in the diagnosis of various brain diseases because the level of local blood flow can be obtained.

CITATION LIST

Patent Literature

Patent Literature 1: Japanese Patent Application Laid-Open No. 2001-112733
Patent Literature 2: Japanese Patent Application Laid-Open No. 2005-237441
Patent Literature 3: Japanese Patent Application Laid-Open No. 2003-199715

Non-Patent Literature

Non-Patent Literature 1: Wen-Ming Luh, et al. QUIPSS II With Thin-Slice TI1 Periodic Saturation: A Method for Improving Accuracy of Quantitative Perfusion Imaging Using Pulsed Arterial Spin Labeling, Magnetic Resonance in Medicine 41: 1246-1254 (1999)
Non-Patent Literature 2: K. J. Friston, J. Ashburner, et al. "Spatial Registration and Normalization of Images" Human Brain Mapping vol. 2, pp. 165-189, 1995
Non-Patent Literature 3: J. Ashburner, P. Neelin, D. L. Collins, A. C. Evans and K. J. Friston, "Incorporating Prior Knowledge into Image Registration", Neuro Image Vol. 6, pp. 344-352, 1997
Non-Patent Literature 4: J. Ashburner and K. J. Friston, "Nonlinear Spatial Normalization using Basis Functions", Human Brain Mapping, vol. 7, pp. 254-266, 1999

SUMMARY OF INVENTION

Problems to be Solved

However, in the PWIs and CBFs that are functional images inputted through the ASL imaging method containing cerebral surface regions that is located outside the cerebral parenchyma, not used for diagnosis of a particular brain disease, often contain high signal values corresponding to a blood flow as noise. Therefore, a physician must correctly determine the region over which the cerebral parenchyma extends in each image, and that results in a problem in that a large burden is placed on the physician during interpretation of the images.

The present invention has been made to solve the above-described conventional problem, and it is an object of the invention to allow functional images of only cerebral parenchyma excluding the cerebral surface to be extracted and displayed in an easy and reliable manner.

Means for Solving the Problems

The present invention according to claim 1 achieves the above object by providing a medical image display processing method comprising the steps of: inputting a functional image in an ASL coordinate system from the head of a subject by an ASL imaging method using an MRI device; subjecting the inputted functional image to mask processing to extract only the region of cerebral parenchyma; and displaying the resultant functional image containing only the extracted region of the cerebral parenchyma, wherein the mask processing for extracting only the region of the cerebral parenchyma is performed using a mask image produced from an ASL-EPI image inputted simultaneously by the ASL imaging method, an MRI morphological image is inputted from the head of the subject using the MRI device, transformation field for transforming from ASL coordinate system of the subject to MRI coordinate system is determined based on the inputted MRI morphological image and the ASL-EPI image, the functional image of only the region of the cerebral parenchyma in the ASL coordinate system is transformed into an image in the MRI coordinate system using the transformation field, and the resultant functional image of the cerebral parenchyma is displayed to be overlaid on the MRI morphological image.

In the present invention according to claim 5, a medical image display processing method comprising the steps of: inputting a functional image in an ASL coordinate system from a head of a subject by an ASL, imaging method using an MRI device; subjecting the inputted functional image to mask processing to extract only a region of cerebral parenchyma; and displaying the resultant functional image containing only the extracted region of the cerebral parenchyma, wherein the mask processing for extracting only the region of the cerebral parenchyma is performed using a mask image produced from an ASL-EPI image inputted simultaneously by the ASL imaging method, determining transformation field for transforming from the ASL coordinate system to standard brain coordinate system based on the ASL-EPI image, and the functional image inputted by the ASL imaging method is transformed into an image in a standard brain coordinate system using the transformation field after the mask processing, and the resultant functional image of only the region of the cerebral parenchyma in the standard brain coordinate system is statistically compared with a pre-prepared functional image of only the region of the cerebral parenchyma of an able-bodied person to produce and display a perfusion weighted Z score map in the standard brain coordinate system.

In the present invention according to claim 6, a medical image display processing method comprising the steps of: inputting a functional image in an ASL coordinate system from a head of a subject by an ASL imaging method using an MRI device; subjecting the inputted functional image to mask processing to extract only a region of cerebral parenchyma; and displaying the resultant functional image containing only the extracted region of the cerebral parenchyma, wherein the mask processing for extracting only the region of the cerebral parenchyma is performed using a mask image produced from an ASL-EPI image inputted simultaneously by the ASL imaging method, determining transformation field for transforming from the ASL coordinate system to standard brain coordinate system based on the ASL-EPI image, and the functional image inputted by the ASL imaging method is transformed into an image in a standard brain coordinate system using the transformation field before the mask processing, and the resultant functional image of only the region of the cerebral parenchyma in the standard brain coordinate system is statistically compared with a pre-prepared functional image of only a region of the cerebral parenchyma of an able-bodied person to produce and display a perfusion weighted Z score map in the standard brain coordinate system.

In the above cases according to claim 5 or 6, the perfusion weighted Z score map in the standard brain coordinate system may be transformed into an image in the ASL coordinate system by inverse transformation and then displayed.

In the present invention according to claim 5 or 6, an MRI morphological image may be inputted from the head of the subject using the MRI device like claim 8, and the inputted MRI morphological image may be subjected to tissue separation to separate a tissue image. The separated tissue image may be transformed into an image in the standard brain coordinate system, and the resultant tissue image transformed in the standard brain coordinate system may be statistically compared with a pre-prepared tissue image of the able-bodied person to produce a brain tissue Z score map in the standard brain coordinate system. The brain tissue Z score map may be displayed together with the perfusion weighted Z score map in the standard brain coordinate system. Further, an MRI morphological image may be inputted from the head of the subject using the MRI device like claim 21, tissue is separated from the inputted MRI morphological image, separated tissue image is transformed into an image in the standard brain coordinate system, statistically compares the resultant tissue image in the standard brain coordinate system with a pre-prepared tissue image of the able-bodied person to produce a brain tissue Z score map in the standard brain coordinate system, and displays the brain tissue Z score map together with the perfusion weighted Z score map in the standard brain coordinate system, and when determining the transformation field for transforming the ASL-EPI image into an image in the standard brain coordinate system based on the ASL-EPI image, a transformation field to transform from the coordinate system of the ASL-EPI image of the subject to a coordinate system of MRI morphological image of the same subject and a transformation field to transform from the coordinate system of MRI morphological image of the subject to the coordinate system of the standard brain are determined respectively, and the transformation field for transforming from the coordinate system of the ASL-EPI image to the coordinate system of the standard brain is determined by combining the two transformation fields. In these cases according to claim 8 or 21, the perfusion weighted Z score map and the brain tissue Z score map in the standard brain coordinate system may be transformed into an image in an MRI coordinate system on the basis of the MRI morphological image and then displayed.

The present invention according to claim 10 achieves the above object by providing a medical image display processing device comprising: image inputting means for inputting a functional image in an ASL coordinate system from the head of a subject by an ASL imaging method using an MRI device; and image processing means for subjecting the inputted functional image to mask processing to extract only the region of cerebral parenchyma, wherein the resultant functional image of only the extracted region of the cerebral parenchyma is displayed, and wherein the image processing means performs the mask processing for extracting only the region of the cerebral parenchyma by using a mask image produced from an ASL-EPI image inputted simultaneously by the ASL imaging method, and an MRI morphological image is inputted from the head of the subject using the MRI device, the image processing means determines transformation field for transforming from the ASL coordinate system of the subject to MRI coordinate system of the subject based on the inputted MRI morphological image and the ASL-EPI image, transforms the functional image of only the region of the cerebral parenchyma in the ASL coordinate system into an image in an MRI coordinate system using the transformation field, and the resultant functional image of the cerebral parenchyma is displayed to be overlaid on the MRI morphological image.

In the present invention according to claim 14, a medical image display processing device comprising: image inputting means for inputting a functional image in an ASL coordinate system from a head of a subject by an ASL imaging method using an MRI device; and image processing means for subjecting the inputted functional image to mask processing to extract only a region of cerebral parenchyma, wherein the resultant functional image of only the extracted region of the cerebral parenchyma is displayed, and wherein the image processing means performs the mask processing for extracting only the region of the cerebral parenchyma by using a mask image produced from an ASL-EPI image inputted simultaneously by the ASL imaging method, and further, the image processing means determines transformation field for transforming from the ASL coordinate system to standard brain coordinate system based on the ASL-EPI image, transforms the functional image inputted by the ASL imaging method into an image in a standard brain coordinate system after the mask processing using the transformation field, and then statistically compares the resultant functional image of only the region of the cerebral parenchyma in the standard brain coordinate system with a pre-prepared functional image of only a region of the cerebral parenchyma of an able-bodied person to produce and display a perfusion weighted Z score map in the standard brain coordinate system.

In the present invention according to claim 15, a medical image display processing device comprising: image inputting means for inputting a functional image in an ASL coordinate system from a head of a subject by an ASL imaging method using an MRI device; and image processing means for subjecting the inputted functional image to mask processing to extract only a region of cerebral parenchyma, wherein the resultant functional image of only the extracted region of the cerebral parenchyma is displayed, and wherein the image processing means performs the mask processing for extracting only the region of the cerebral parenchyma by using a mask image produced from an ASL-EPI image inputted simultaneously by the ASL imaging method, and further, the image processing means determines transformation field for transforming from the ASL coordinate system to standard brain coordinate system based on the ASL-EPI image, transforms the functional image inputted by the ASL imaging method into an image in a standard brain coordinate system before the mask processing using the transformation field, and then statistically compares the resultant functional image of only the region of the cerebral parenchyma in the standard brain coordinate system with a pre-prepared functional image of only a region of the cerebral parenchyma of an able-bodied person to produce and display a perfusion weighted Z score map in the standard brain coordinate system.

In the above cases according to claim 14 or 15, the image processing means may transform the perfusion weighted Z score map in the standard brain coordinate system into an image in the ASL coordinate system by inverse transformation and then display the resultant perfusion weighted Z score map.

In the present invention according to claim 14 or 15, an MRI morphological image may be inputted from the head of the subject using the MRI device like claim 17. The image processing means may perform tissue separation on the inputted MRI morphological image to separate a tissue image, transform the separated tissue image into an image in the standard brain coordinate system, statistically compare the resultant tissue image in the standard brain coordinate system with a pre-prepared tissue image of the able-bodied person to produce a brain tissue Z score map in the standard brain coordinate system, and display the brain tissue Z score map together with the perfusion weighted Z score map in the standard brain coordinate system. Further, an MRI morphological image may be inputted from the head of the subject using the MRI device like claim 23, the image processing means conduct tissue separation from the inputted MRI morphological image, transforms the separated tissue image into an image in the standard brain coordinate system, statistically compares the resultant tissue image in the standard brain coordinate system with a pre-prepared tissue image of an able-bodied person to produce a brain tissue Z score map in the standard brain coordinate system, and displays the brain tissue Z score map together with the perfusion weighted Z score map in the standard brain coordinate system and when determining the transformation field for transforming the ASL-EPI image into an image in the standard brain coordinate system based on the ASL-EPI image, determines a transformation field for transforming from the coordinate system of the ASL-EPI image of the subject to a coordinate system of MRI morphological image of the same subject and a transformation field for transforming from the coordinate system of MRI morphological image of the subject to the coordinate system of the standard brain respectively, and determines the transformation field for transforming the ASL-EPI image to the coordinate system of the standard brain by combining the two transformation fields. In these cases according to claim 17 or 23, the image processing means may transform the perfusion weighted Z score map and the brain tissue Z score map into images in the standard brain coordinate system in an MRI coordinate system on the basis of the MRI morphological image and display the resultant maps.

The present invention according to claim 25 also provides a computer readable program for executing a medical image display processing method on a computer.

Effects of Invention

According to the present invention, the region of cerebral parenchyma can be easily and reliably extracted from a functional image inputted by the ASL imaging method, and the resultant image can be displayed. Therefore, only the blood flow in the brain can be observed. Accordingly, a burden on a health professional such as a physician during interpretation of the image can be reduced, and useful diagnosis-assisting information can be provided to the health professional.

BRIEF DESCRIPTION OF DRAWINGS

FIG. 4 is a set of diagrams illustrating an example of a method of producing a mask image.

FIG. 5 is a set of diagrams illustrating another example of the method of producing the mask image.

FIG. 11 is a set of diagrams illustrating the images of Z score maps of a standard brain and the brain of a subject.

FIG. 12 is a set of diagrams illustrating the concepts of inverse transformation fields formed by spatial normalization.

DESCRIPTION OF EMBODIMENTS

Embodiments of the present invention will next be described in detail with reference to the drawings.

Figure 1:
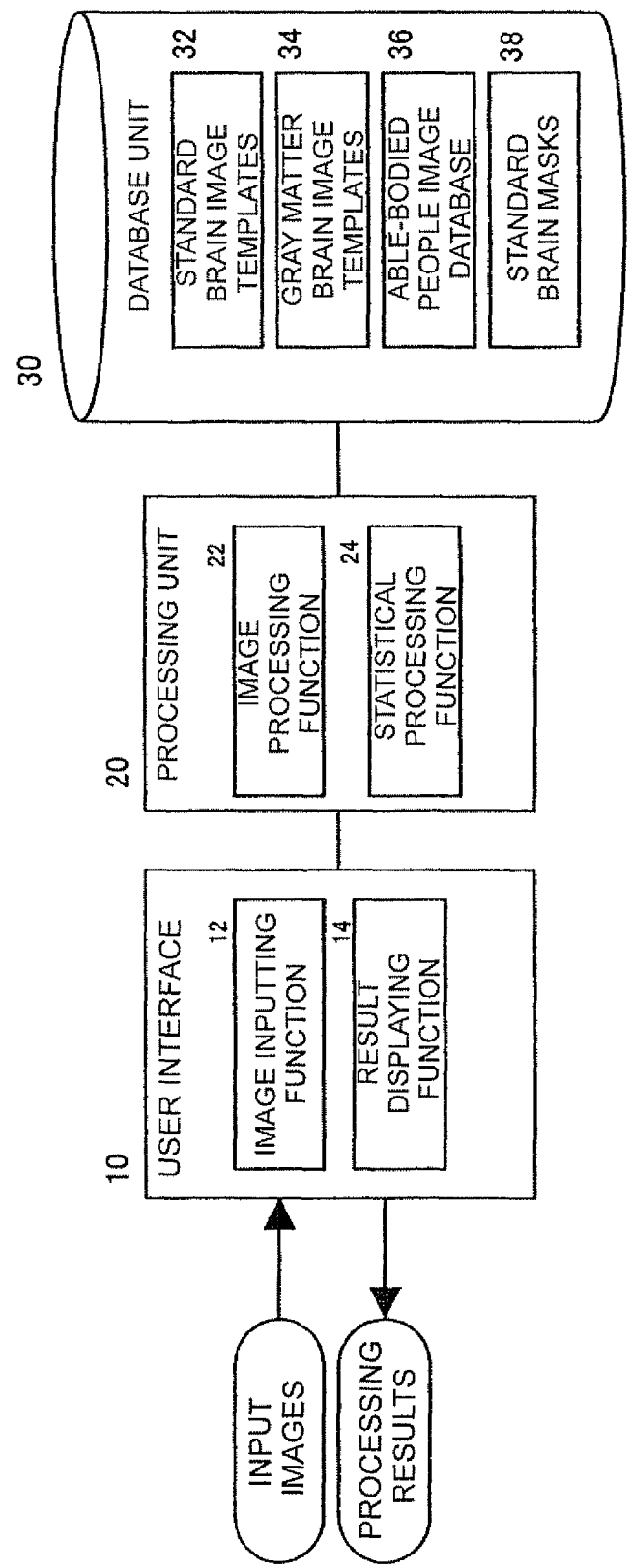
FIG. 1 is a block diagram illustrating a main part of a medical image display processing device in one embodiment according to the present invention.

FIG. 1 is a block diagram illustrating a main part of a medical image display processing device in one embodiment according to the present invention.

The medical image display processing device of the present embodiment includes a user interface 10, an image-statistical processing unit 20, and a database unit 30. The user interface 10 has an image inputting function 12 for inputting input images from an MRI device and a result displaying function 14 for displaying the results of program-processing performed by the processing unit 20 on a display. The processing unit 20 has an image processing function 22 for processing MRI morphological images, perfusion weighted images, and ASL-EPI images to be described later, inputted from the user interface 10, and a statistical processing function 24 for performing, for example, various statistical computations. Standard brain image templates 32, gray matter brain image templates 34, an able-bodied person image database 36, standard brain masks 38, etc. that are used for processing, to be described later, by the processing unit 20 have been stored in the database unit 30.

Figure 2:
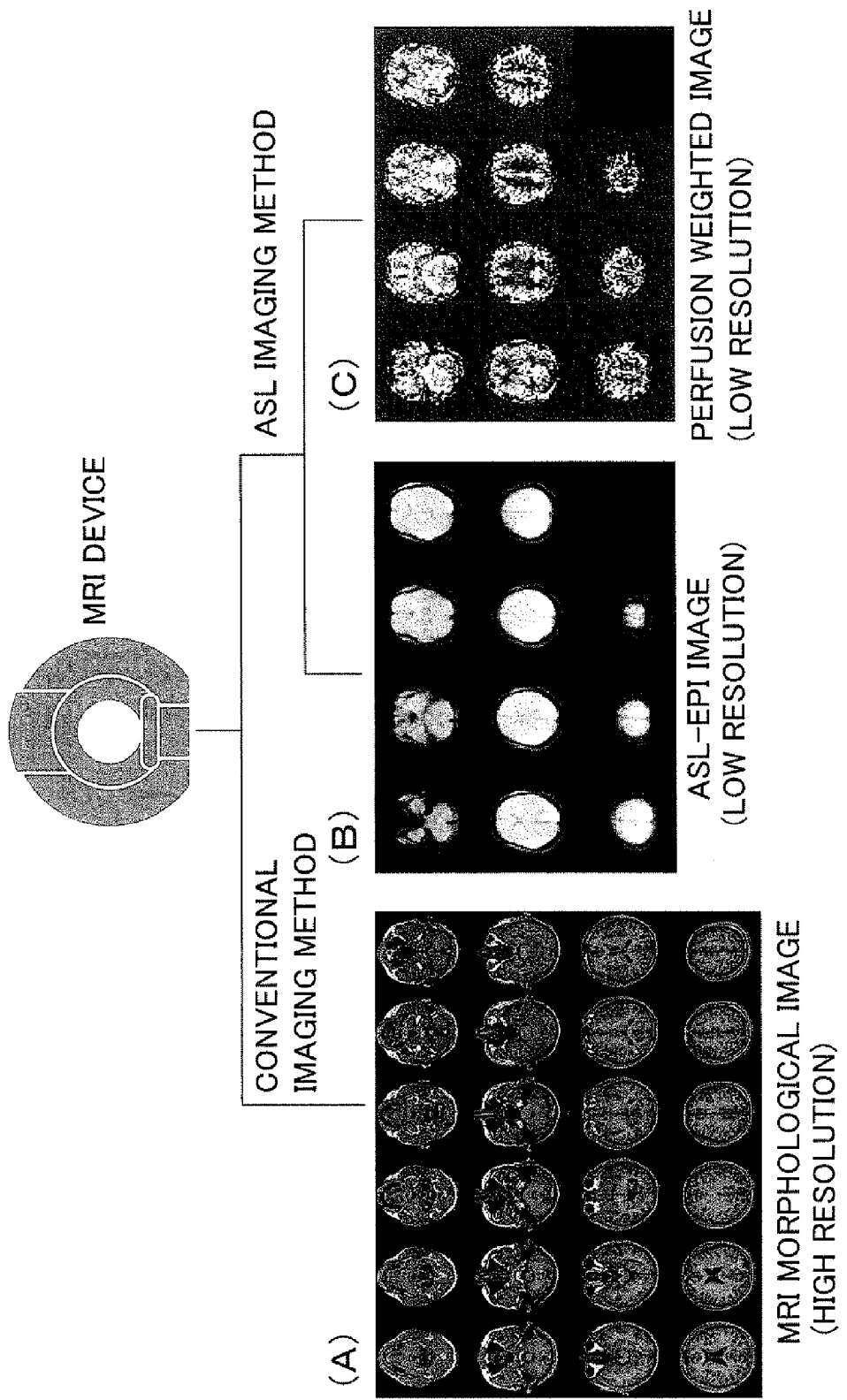
FIG. 2 is a diagram illustrating the features of images inputted to the medical image display processing device.

In the medical image display processing device in the present embodiment, as shown conceptually in FIG. 2, MRI morphological images (A) taken by a conventional imaging method, ASL-EPI images (B) being low-resolution morphological images and taken by the ASL imaging method, and perfusion weighted images (C) being functional images and taken by the ASL imaging method are inputted from the MRI device.

Figure 3:
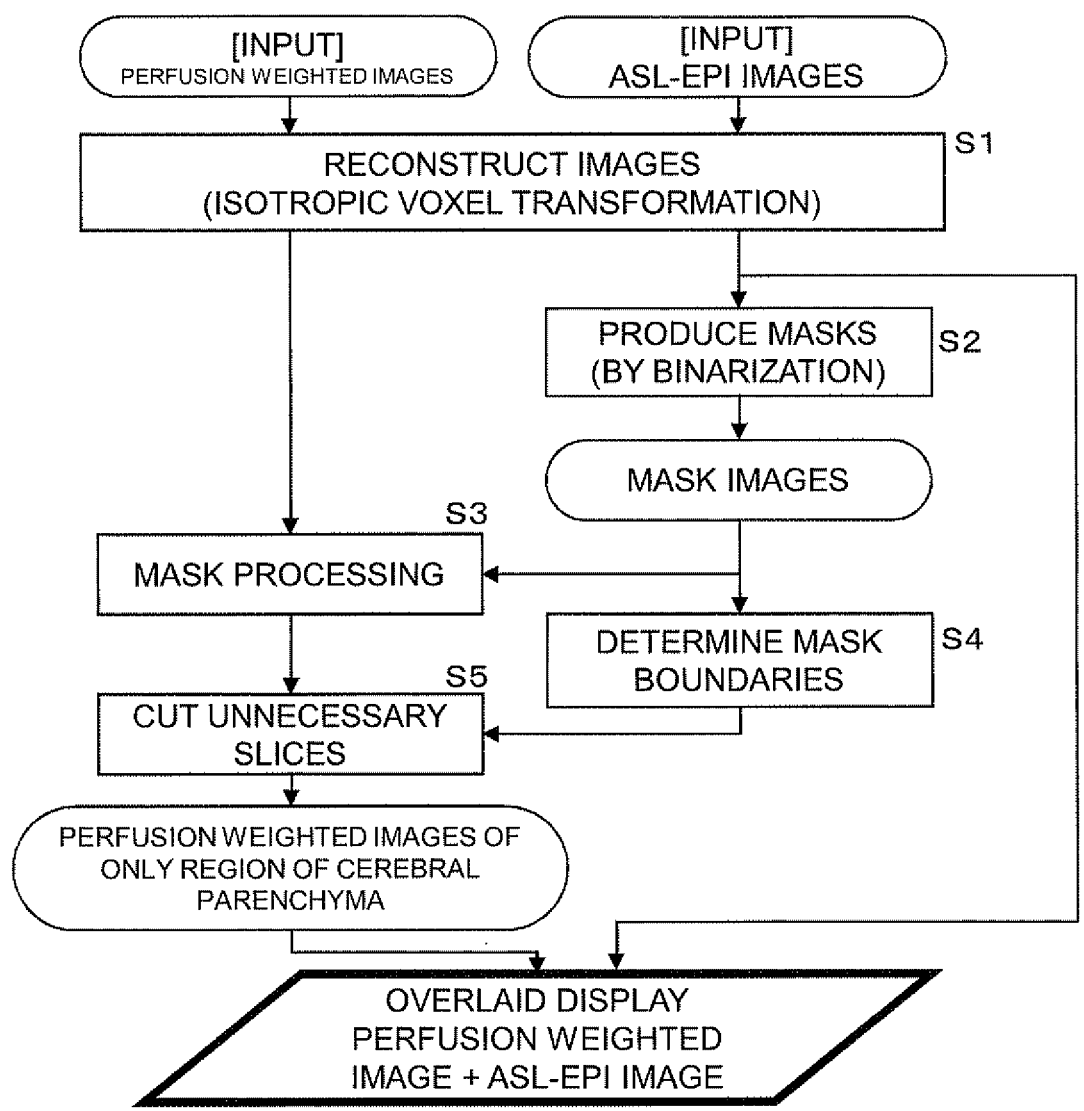
FIG. 3 is a flowchart showing the basic processing procedures applied to a medical image display processing method of a first embodiment according to the present invention.

Next, basic processing procedures applied to an image display processing method of a first embodiment according to the present invention that is performed by the medical image display processing device will be described with reference to a flowchart shown in FIG. 3. In this flowchart, each ellipse represents an image or a processed product.

In the present embodiment, perfusion weighted images and ASL-EPI images are inputted as input images.

First, the two types of inputted images are subjected to image reconstruction (step 1). The image reconstruction is a process, in which the two types of images are re-sampled three-dimensionally and divided into voxels with equal size in all directions to make the units of the three-dimensional voxels, corresponding to pixels in two-dimensions, of the two types of images the same size.

Next, mask images are produced from the ASL-EPI images by mask production (step 2).

FIG. 4 shows a mask image (B) produced by binarizing the ASL-EPI image (A) on the upper side.

The mask image is produced from the ASL-EPI image to mask regions of the perfusion weighted image other than the region of the cerebral parenchyma. The low-resolution ASL-EPI image has characteristics that the pixel values in the region of the cerebral parenchyma are higher than those of the other regions. Such characteristics are used to perform binarization by thresholding to thereby produce a mask image in which the pixel values in the region of the cerebral parenchyma are set to 1 and the pixel values in the other regions are set to 0 (mask). The threshold value may be a predetermined fixed value or may be adaptively determined using, for example, the Otsu binarization algorithm.

To produce a mask image from an ASL-EPI image, a method shown in FIG. 5 may be used. With this method, a mask image can be obtained with higher precision as compared to the method shown in FIG. 4. More specifically, a low-resolution ASL-EPI image shown in FIG. 5(A) is subjected to tissue separation processing to extract regions of white matter, gray matter, and cerebrospinal fluid, and the regions of the white matter and gray matter are combined and binarized, as shown in FIG. 5(B). Then filling processing is performed to obtain a mask image shown in FIG. 5(C). The threshold value is set in the same manner as in FIG. 4.

The mask images produced by any of the above methods are applied to the perfusion weighted images, which are functional images, to perform mask processing (step 3).

The mask processing is applied to the perfusion weighted images in (C) of FIG. 2 that have been subjected to the above step 1. The mask processing is performed on each slice image, and the voxel values in regions other than the region of the cerebral parenchyma are set to 0.

Next, mask boundaries are determined using the mask images produced in the above step 2 (step 4), and unnecessary slices are cut from the perfusion weighted images subjected to the mask processing in the above step 3 (step 5).

Figure 6:
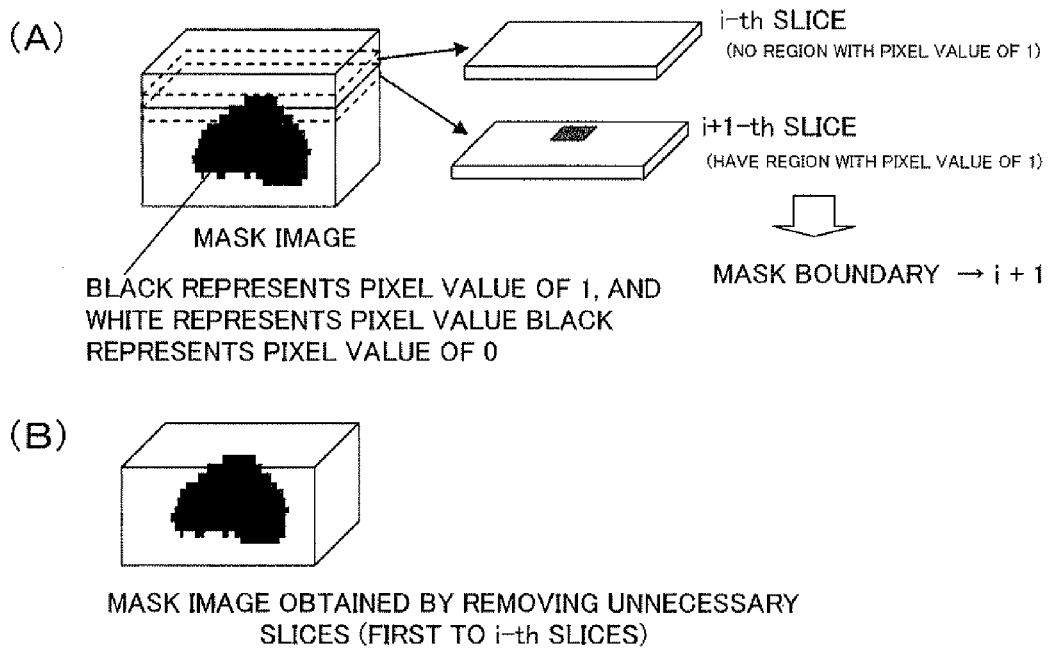
FIG. 6 is a set of diagrams illustrating a mask boundary and a method of determining the mask boundary.

The determination of the mask boundaries will be described with reference to FIG. 6. FIG. 6(A) is a perspective view of the produced mask images. The black color represents a pixel value of 1, and the white color represents a pixel value of 0.

The determination of the mask boundaries is a processing for removing vertical and horizontal slices not containing the region of the cerebral parenchyma (the region with a pixel value of 1) from the mask images. In this drawing, the i+1-th slice that is a first slice containing the region with a pixel value of 1 in a downward direction from the upper edge is determined as a mask boundary, and the first to i-th slices are determined as unnecessary slices and cut away to form mask images shown in FIG. 6(B). On the upper edge, the produced perfusion weighted image contains only the region of the cerebral parenchyma. This procedure is repeated for all the vertical and horizontal directions, and the slices of the perfusion weighted images can thereby be defined only by the remaining slices of the mask images. When the positions of the head in the images are known in advance, the mask boundaries may be determined by removing a predetermined number of slices that is set in advance.

Figure 7:
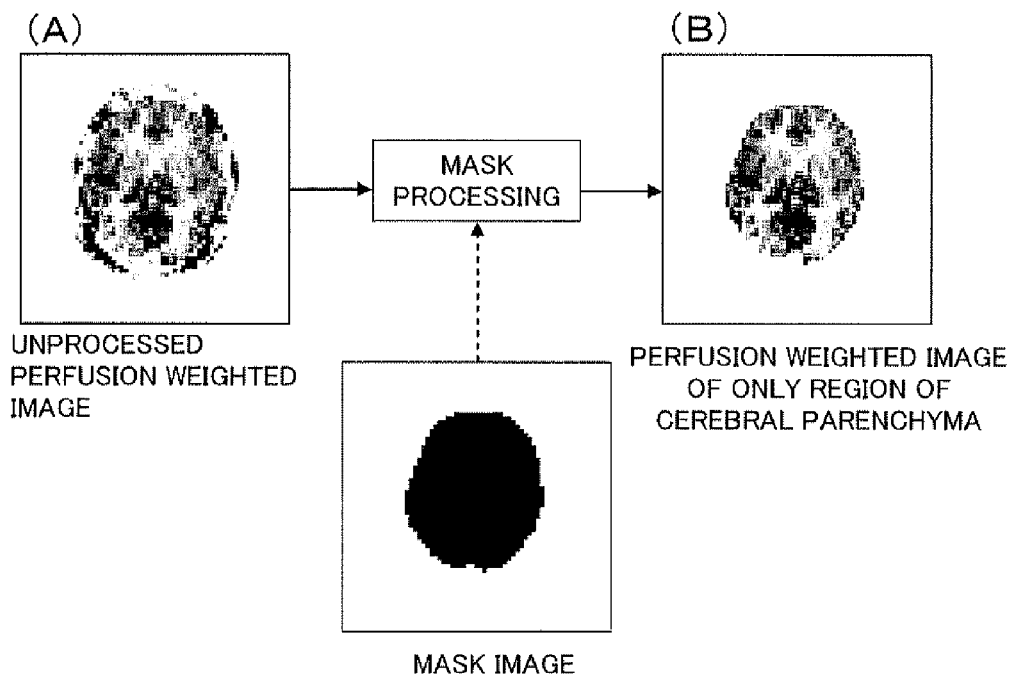
FIG. 7 is a diagram illustrating a method of extracting a perfusion weighted image of only the region of cerebral parenchyma by mask processing.

By performing the mask processing in the manner described above, i.e., by subjecting an unprocessed perfusion weighted image having blurred circumferential edges shown in FIG. 7(A) to the mask processing using a mask image, a perfusion weighted image including only the extracted region of the cerebral parenchyma can be produced, as shown in FIG. 7(B). Therefore, only the region of the cerebral parenchyma in a perfusion weighted image can be displayed on the display using the result displaying function 14, and an ASL-EPI image can be overlaid on the displayed perfusion weighted image. Therefore, diagnosis-assisting information quite useful for health professionals can be provided.

Figure 8:
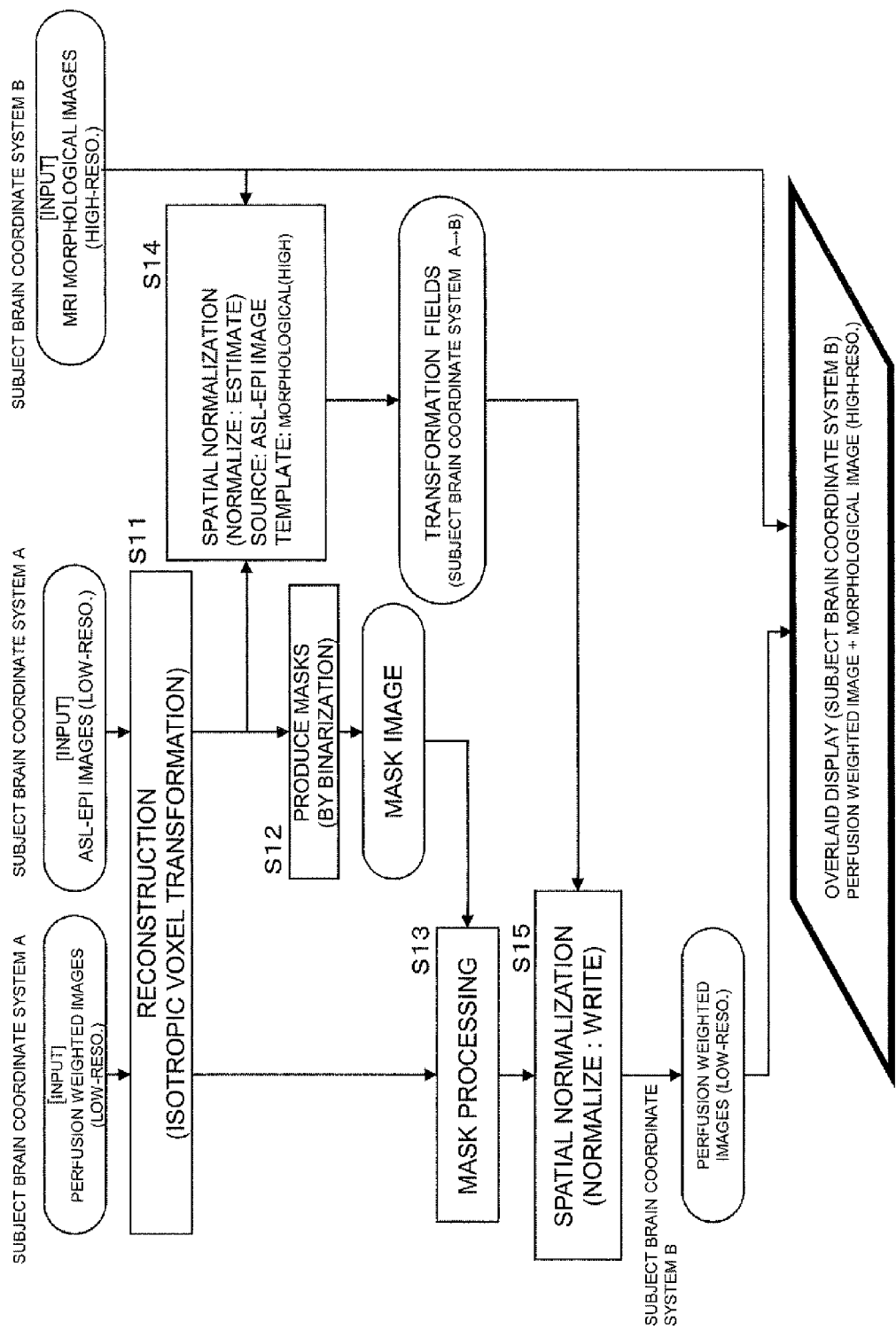
FIG. 8 is a flowchart showing the processing procedure in a medical image display processing method of a first embodiment according to the present invention.

Next, an image display processing method of this embodiment will be described with reference to a flowchart shown in FIG. 8.

The present embodiment is the same as the basic processing procedures described with reference to the flowchart in FIG. 3 in that low-resolution (abbreviated as Low-Reso. in the figure) perfusion weighted images and low-resolution ASL-EPI images taken by the ASL method are inputted as input images. However, high-resolution (abbreviated as High-Reso. in the figure) MRI morphological images taken by a conventional method are also used as input images.

These images taken by the ASL method and the conventional method are inputted from the head of a single subject. The ASL-EPI images by the former method are taken in the same sequence as that for the perfusion weighted images, and therefore the positions in these images completely match each other. However, the MRI morphological images by the latter method are taken in a sequence continuous with the sequence for the ASL method or in a different sequence, and therefore the positions and angles in the MRI morphological images may be different from those in the ASL-EPI and perfusion weighted images. Therefore, to distinguish the coordinate systems for these images, the coordinate system used in the former method is referred to as an ASL coordinate system or a subject brain coordinate system A (hereinafter may be referred to as a coordinate system A), and the coordinate system used in the latter method is referred to as an MRI coordinate system or a subject brain coordinate system B (hereinafter may be referred to as a coordinate system B).

In the flowchart, the processing in steps 11 to 13 is the same as the processing in the above steps 1 to 3, and the description thereof will be omitted.

In the present embodiment, the determination of mask boundaries and elimination of unnecessary slices performed in steps 4 and 5 of the basic processing procedures and the perfusion weighted images produced thereby are omitted from the figure. However, perfusion weighted images of only the regions of the cerebral parenchyma are extracted in the coordinate system A (ASL coordinate system) by mask processing in step 13. The coordinate system for the MRI morphological images is the coordinate system B (MRI coordinate system).

To compensate for the positional and angular differences, a transformation field for transformation from the coordinate system A to the coordinate system B is estimated using spatial normalization in which an ASL-EPI image is fitted to an MRI morphological image used as a template (step 14). Herein, the estimation of the transformation field is to estimate linear transformation and nonlinear transformation parameters for the ASL-EPI image that minimize the sum of squares of errors between the ASL-EPI images and the MRI morphological images. For example, any of methods described in Non-Patent Literatures 2, 3, and 4 can be used.

When the spatial normalization is performed on images of a single subject as in step 14, registration is the purpose of the spatial normalization, and therefore linear transformation, particularly only translation and rotation (rigid body transformation), is used. However, when the brain of the subject is transformed to a standard brain as in steps 24, 32, 52, and 72 described later, registration and deformation are necessary, and linear transformation and nonlinear transformation are performed.

Next, the perfusion weighted images in the coordinate system A that have been extracted and produced by the mask processing (these images are omitted from the figure) are transformed into images in the coordinate system B for the MRI morphological images by the spatial normalization using the transformation fields (step 15). The term "Normalize:Write" in the figure means that the estimated transformation field is used to transform an image.

Figure 9:
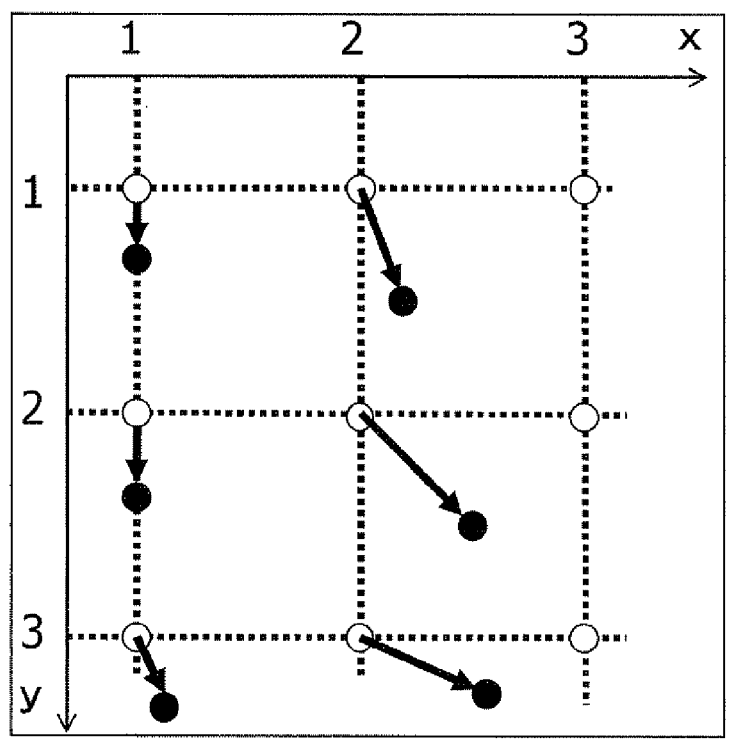
FIG. 9 is a diagram illustrating the concept of a transformation field formed by spatial normalization.

The transformation field used here means a transformation matrix determined by fitting an ASL-EPI image to an MRI morphological image used as a template. As FIG. 9 shows its image, the transformation field is represented as a set of three-dimensional vectors that indicate displaced coordinate positions obtained by the transformation of the original coordinate positions. In this figure, two-dimensional representation is used for simplicity. The basic principles of other various transformation fields used later are the same as the above principle.

According to the present embodiment described above, the perfusion weighted images containing the extracted regions of the cerebral parenchyma can be displayed to be overlaid on the high-resolution MRI morphological images correctly. Therefore, the perfusion weighted images can be displayed together with more clearly displayed cranium regions in position, and more useful information can be provided.

Figure 10:
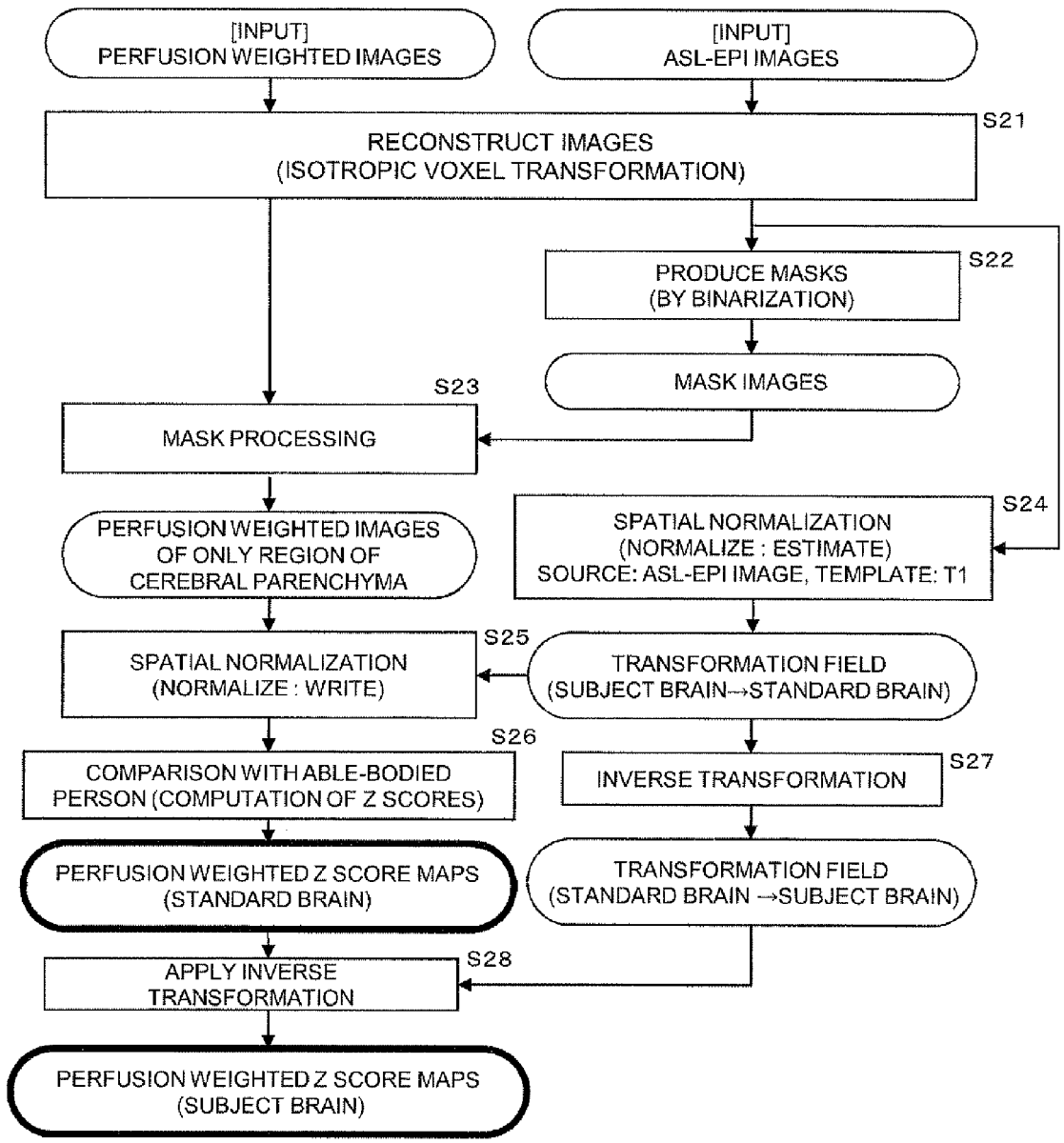
FIG. 10 is a flowchart showing the processing procedure in a medical image display processing method of a second embodiment according to the present invention.

Next, an image display processing method of a second embodiment will be described with reference to a flowchart shown in FIG. 10.

In the present embodiment, as in the basic processing procedures, perfusion weighted images and ASL-EPI images are used as input images, and the same processing as in the above steps 1 to 4 is used to produce perfusion weighted images of only the region of the cerebral parenchyma (steps 21 to 23). However, the processing related to the determination of mask boundaries is omitted from the figure.

In the present embodiment, each of the perfusion weighted images in the subject brain coordinate system A that have been produced in step 23 is transformed into an image in the standard brain coordinate system. First, a spatial transformation field used to transform an ASL-EPI image into an image on the standard brain is estimated using spatial normalization in which the ASL-EPI image is fitted to a T1 weighted image serving as a template and stored in the database unit 30 as a standard brain image template 32 (step 24).

Next, the transformation field formed by estimation is used to perform the spatial normalization to transform the perfusion weighted image in the coordinate system A into an image in the standard brain coordinate system (step 25).

Each perfusion weighted image that contains only the region of the cerebral parenchyma transformed in the standard brain coordinate system is compared with the data of perfusion weighted images in the able-bodied people image database 36 stored in the database unit 30. Then the voxel values in the entire perfusion weighted image that represent the intensity of perfusion (blood flow) are converted to statistical values (Z scores) indicating the degree of deviation from the intensity of perfusion in an able-bodied person to produce a perfusion weighted Z score map on the standard brain (step 26). The image of the perfusion weighted Z score map is shown in FIG. 11(A).

The Z, score is a statistic indicating the deviation of a sample value x from the mean of the population and can be represented by $$Z \text{ score} = (\text{mean} - x)/\sigma$$

wherein σ is the standard deviation of the population (see, for example, Patent literature 2).

Next, an inverse transformation field used for transformation from the standard brain coordinate system to the subject brain coordinate system A is generated by the inverse transformation of the transformation field formed in the above step 24 (step 27). Then the inverse transformation field is applied to the perfusion weighted Z score map in the standard brain coordinate system to generate a perfusion weighted Z score map in the subject brain coordinate system that is exaggeratedly illustrated in FIG. 11(B) (step 28).

The inverse transformation field used here will be described with reference to FIG. 12.

Suppose that, for convenience, a forward transformation field f shown by arrows (solid lines) in FIG. 12(A) is the same as that in FIG. 9. When an inverse transformation field g of the forward transformation field f is determined, a coordinate system in which the values of coordinates (filled circles) transformed by the forward transformation field f are replaced with the values of the original coordinates (open circles) is generated as shown in FIG. 12(B). Then the coordinate values of the original coordinate positions (open circles) are determined by linear interpolation. These coordinate values represent the inverse transformation g of the forward transformation f with the original coordinate values used as reference. More specifically, in the coordinate system for the lattice points represented by the filled circles, the coordinates (x, y) of lattice points represented by open triangles are determined by linear interpolation and used as inverse-transformed coordinate values. The (inverse) transformation field g is represented by arrows (dotted lines).

In one conventional method used to observe the levels of blood flow in different sites based on a brain atlas, the brain images of a subject are transformed into an image on a standard brain using anatomical normalization (spatial normalization) corresponding to the above-described spatial normalization (see, for example, Patent Literature 3).

In this method, the blood flow images themselves are fitted to standard brain templates by anatomical normalization. However, as described above, the region of the cerebral surface may contain blood flow values (signals) due to noise, and the skull may have a wide region in which the blood flow level is low because of, for example, infract. In such cases, the shape of the brain is significantly different from the shape of the standard brain templates, and this causes a problem in that the precision of the anatomical normalization deteriorates. In the present embodiment, since the perfusion weighted images of only the region of the cerebral parenchyma are transformed into images in the standard brain coordinate system, such a problem does not occur. Therefore, high-precision anatomical normalization of perfusion weighted images can be achieved.

In the present embodiment described above, the perfusion weighted images of only the region of the cerebral parenchyma can be displayed. Additionally, in the perfusion weighted images, a region in which the level of blood flow is significantly lower than that in the able-bodied person can be specified. In addition, since the output is obtained in two coordinate systems including the coordinate system for the standard brain and that for the subject brain (original images), useful diagnosis-assisting information can be provided.

Figure 13:
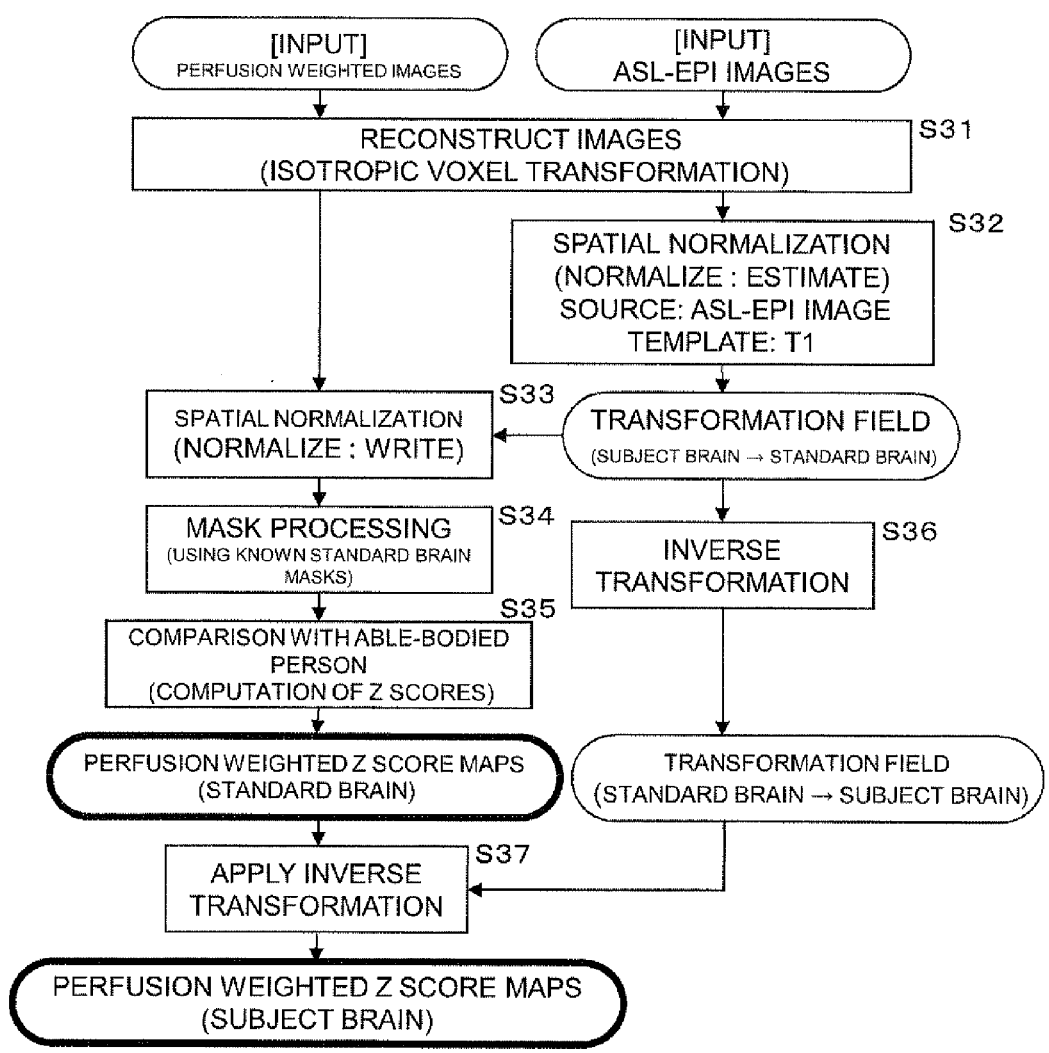
FIG. 13 is a flowchart showing the processing procedure in a medical image display processing method of a third embodiment according to the present invention.

Next, an image display processing method of a third embodiment will be described with reference to a flowchart shown in FIG. 13.

In the present embodiment, perfusion weighted images and ASL-EPI images are used as input images, and the process until image reconstruction in step 31 is the same as that in the second embodiment. However, transformation fields to the standard brain are first formed from the reconstructed ASL-EPI images using spatial normalization in the same manner as in the above step 24 (step 32), and the transformation fields are applied to the perfusion weighted images before mask processing to transform them into images in the standard brain coordinate system (step 33).

Next, the perfusion weighted images transformed into the standard brain are subjected to mask processing using the known standard brain masks 38 stored in the database unit 30 (step 34).

Although not illustrated, perfusion weighted images of only the region of the cerebral parenchyma are extracted by the mask processing, as in the second embodiment. Since these images have been transformed into the standard brain, they can be directly compared with the images of the able-bodied person to produce Z score maps for the perfusion weighted images. Then inverse transformation fields are produced by inverse transformation similar to that in the above step 27 described above (step 36), and the produced inverse transformation fields are applied to the Z score maps on the standard brain to produce Z score maps in the subject brain coordinate system (step 37).

According to the present embodiment described above, the precision of transformation to the standard coordinate system is slightly lower than that when the mask images produced from the ASL-EPI images are used. However, the mask processing can be performed using the existing standard brain masks in a simple manner, and the same effects as in the third embodiment can be obtained.

Figure 14:
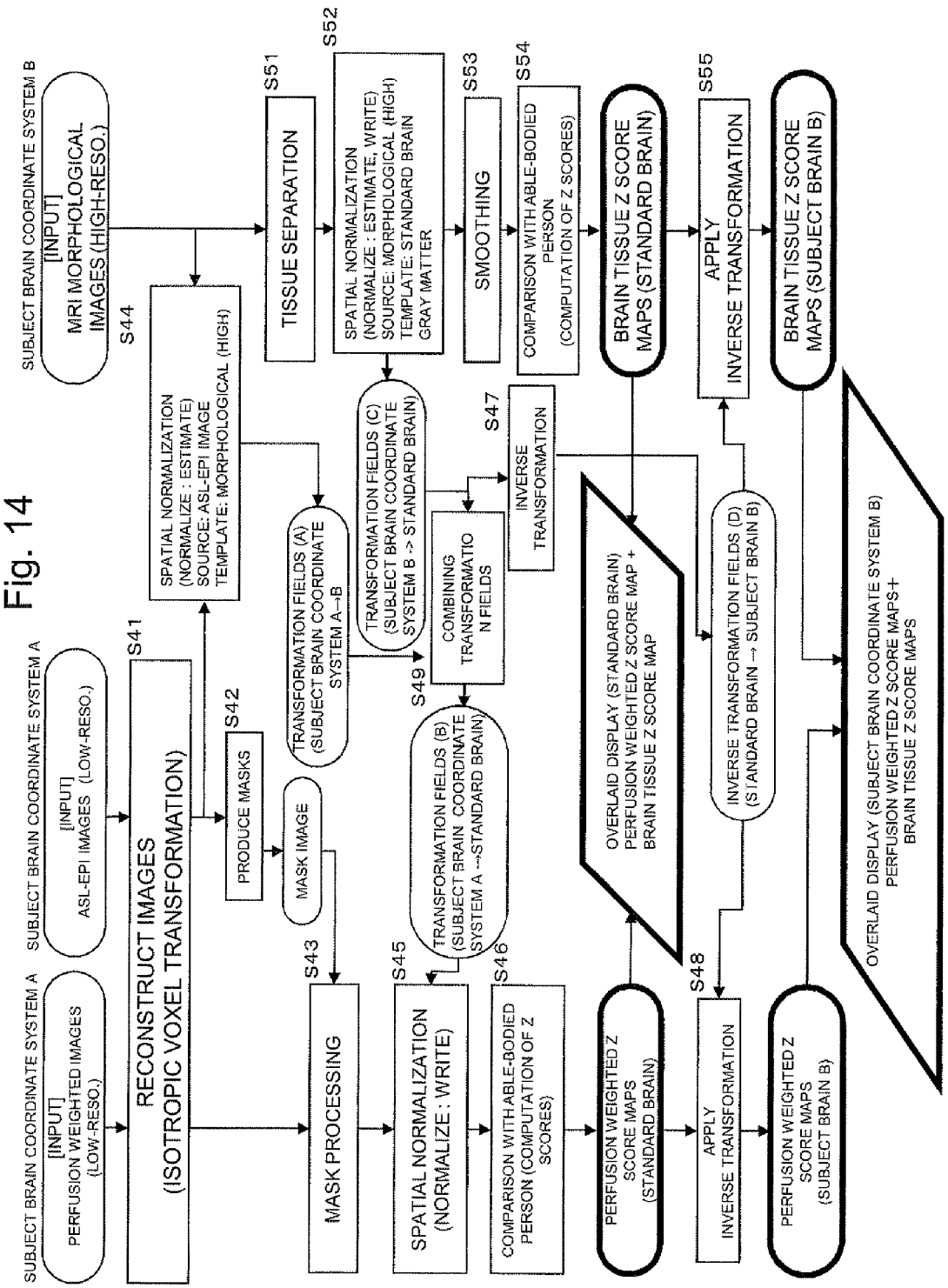
FIG. 14 is a flowchart showing the processing procedure in a medical image display processing method of a fourth embodiment according to the present invention.

Next, a fourth embodiment will be described with reference to a flowchart shown in FIG. 14.

In the image display processing method of the present embodiment, as in the first embodiment, the input images also include MRI morphological images in the coordinate system B. However, the processing from image reconstruction in step 41 to the application of inverse transformation in step 48 is basically the same as the processing in steps 21 to 28 in the second embodiment, although the perfusion weighted images produced by the mask processing in step 43 are omitted. However, since Z score maps are transformed into an image in the coordinate system B by the inverse transformation in step 48, the configuration of the inverse transformation fields applied is different. This will be described later.

In the present embodiment, in addition to the perfusion weighted Z score maps described above, the degree of atrophy of brain tissues can be displayed as Z score maps based on the MRI morphological images inputted by the conventional method.

More specifically, first, the MRI morphological images in the subject brain coordinate system B are subjected to tissue separation (step 51). The tissue separation preformed here is separation of the white matter and gray matter from the T1 weighted images. The sizes and shapes of the separated tissues are fitted to those of the standard brain by spatial normalization (step 52). A template "gray.mnc" used for the normalization means a standard brain template of the gray matter.

The normalized tissue images are smoothened for, for example, removal of noise (step 53) and then compared with the tissue image data of the able-bodied person to compute Z scores indicating the degree of atrophy of the brain tissues for the entire tissue images, and Z score maps in the standard brain coordinate system are thereby generated (step 54).

The details of the processing in steps 51 to 54 have been described in Patent Literature 2 mainly for the gray matter. The produced brain tissue Z score maps on the standard brain can be displayed together with the perfusion weighted Z score maps on the standard brain produced in the above step 46.

In the present embodiment, the standard brain Z score maps produced by comparison with the brain of the able-bodied person in step 54 are transformed into an image in the coordinate system B by inverse transformation (step 55), and the brain tissue Z score maps in the coordinate system B can be displayed together with the perfusion weighted Z score maps in the coordinate system B generated by inverse transformation in the above step 48.

To realize the above-described processing, the present embodiment uses transformation fields (A) for converting the subject brain coordinate system A to the subject brain coordinate system B, transformation fields (B) for converting the subject brain coordinate system A to the standard brain, transformation fields (C) for converting the subject brain coordinate system B to the standard brain, and inverse transformation fields (D) for converting the standard brain to the coordinate system B.

The transformation fields (A) are formed by spatial normalization in step 44. The transformation fields (B) applied in the above step 45 are formed in step 49 by combining the transformation fields (A) and the transformation fields (C) formed by spatial normalization in the above step 52. The inverse transformation fields (D) applied for the inverse transformation in the above steps 48 and 55 are formed by inverse transformation of the transformation fields (C) in step 47.

In the embodiment described above, a region in which distributions in the perfusion and morphology are significantly lower than those of the able-bodied person can be specified. The significant reduction in distribution in the perfusion weighted images means a reduction in blood flow, and the significant reduction in distribution in the MRI morphological images means atrophy. These can be outputted in two coordinate systems including a coordinate system for the standard brain and that for the subject brain (original images) and can be displayed in the same coordinate system in an overlaid manner.

Figure 15:
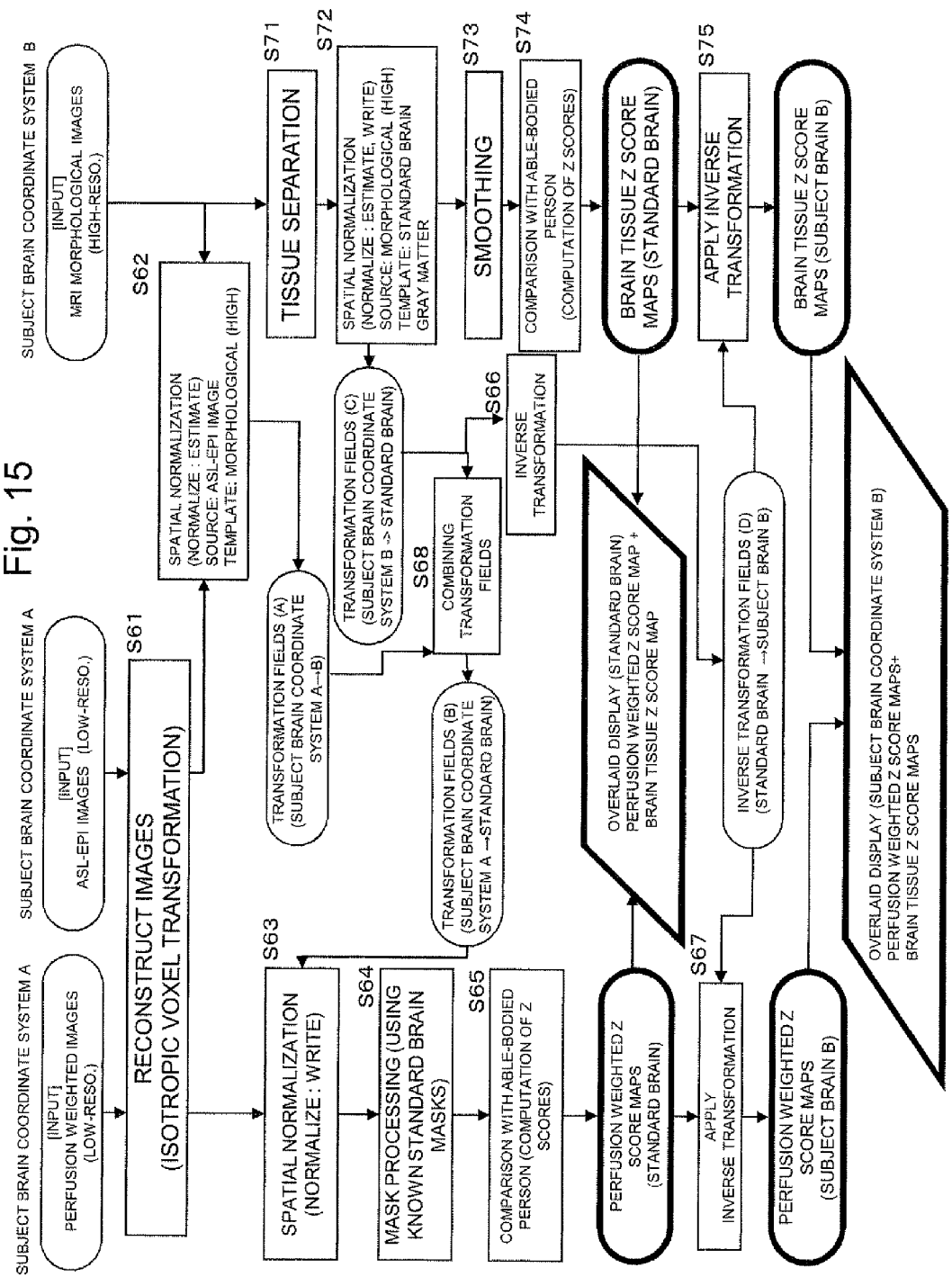
FIG. 15 is a flowchart showing the processing procedure in a medical image display processing method of a fifth embodiment according to the present invention.

Next, a fifth embodiment will be described with reference to a flowchart shown in FIG. 15.

The present embodiment is substantially the same as the fourth embodiment except that, as in the third embodiment, the perfusion weighted images are first transformed into an image on the standard brain by spatial normalization in which the transformation fields (B) are applied (step 63) and then mask processing is performed using the known standard brain Z masks (step 64). Therefore, steps 65 and 67 are the same as steps 46 and 48 in FIG. 14, and the respective processings in steps 71 to 75 for tissue separation are the same as the processings in steps 51 to 55 described above. In addition, all the (inverse) transformation fields are the same as those in the fourth embodiment, and the description thereof will be omitted.

According to the present embodiment, the mask processing is simplified as in the third embodiment, and the same effects as those in the fourth embodiment can be obtained.

In the medical image display processing device in each embodiment described above, the perfusion weighted images outputted by the ASL imaging method and the MRI morphological images can be registered with high precision (positioning). In addition, various images can be overlaid and displayed, such as images in the standard brain coordinate system including the standard brain morphological images, standard brain blood flow images, morphological image Z score maps, and perfusion weighted Z score maps, and images in the subject brain coordinate system including the subject brain morphological images, subject brain perfusion weighted images, inverse-transformed morphological Z score maps, and inverse-transformed perfusion weighted Z score maps. Therefore, various types of diagnosis assistance can be provided using the morphological images and the functional images.

In the above embodiments, when the perfusion weighted images inputted by the ASL imaging method are transformed into an image in the standard brain coordinate system before the mask processing, it is described that the mask processing is performed using the standard brain mask, but this is not a limitation. The ASL-EPI images inputted simultaneously with the perfusion weighted images may also be transformed into an image in the standard brain coordinate system, and mask images produced from the resultant ASL-EPI images may be used.

In the above description, the perfusion weighted images are inputted as functional images, but this is not a limitation. CBFs may be inputted. In such a case, images of absolute cerebral blood flows are obtained as result images.

INDUSTRIAL APPLICABILITY

The present invention is useful as a medical image display processing method, device, and program used when brain images inputted through MRI (Magnetic Resonance Imaging) are subjected to image processing to assist the diagnosis of brain diseases.

REFERENCE SIGNS LIST 10 user interface
20 image-statistical processing unit
30 database unit
32 standard brain image template
34 gray matter brain image template
36 able-bodied person image database
38 standard brain mask

The invention claimed is:
1. A medical image display processing method comprising the steps of:
inputting a functional image in an ASL coordinate system from a head of a subject by an ASL imaging method using an MRI device;
subjecting the inputted functional image to mask processing to extract only a region of cerebral parenchyma; and
displaying the resultant functional image containing only the extracted region of the cerebral parenchyma,
wherein the mask processing for extracting only the region of the cerebral parenchyma is performed using a mask image produced from an ASL-EPI image inputted simultaneously by the ASL imaging method, an MRI morphological image is inputted from the head of the subject using the MRI device, transformation field from ASL coordinate system of the subject to MRI coordinate system is determined based on the inputted MRI morphological image and the ASL-EPI image, the functional image of only the region of the cerebral parenchyma in the ASL coordinate system is transformed into an image in the MRI coordinate system using the transformation field, and the resultant functional image of the cerebral parenchyma is displayed to be overlaid on the MRI morphological image.

2. A computer readable program, embodied on a non-transitory computer readable medium, for executing the medical image display processing method according to claim 1 on a computer.

3. A medical image display processing method comprising the steps of:
inputting a functional image in an ASL coordinate system from a head of a subject by an ASL imaging method using an MRI device;
subjecting the inputted functional image to mask processing to extract only a region of cerebral parenchyma; and
displaying the resultant functional image containing only the extracted region of the cerebral parenchyma,
wherein the mask processing for extracting only the region of the cerebral parenchyma is performed using a mask image produced from an ASL-EPI image inputted simultaneously by the ASL imaging method,
determining transformation field from the ASL coordinate system to standard brain coordinate system based on the ASL-EPI image, and the functional image inputted by the ASL imaging method is transformed into an image in a standard brain coordinate system using the transformation field after the mask processing, and the resultant functional image of only the region of the cerebral parenchyma in the standard brain coordinate system is statistically compared with a pre-prepared functional image of only the region of cerebral parenchyma of an able-bodied person to produce and display a perfusion weighted Z score map in the standard brain coordinate system.

4. The medical image display processing method according to claim 3, wherein the perfusion weighted Z score map in the standard brain coordinate system is transformed into an image in the ASL coordinate system by inverse transformation and then the transformed image is displayed.

5. The medical image display processing method according to claim 3, wherein an MRI morphological image is inputted from the head of the subject using the MRI device, the inputted MRI morphological image is subjected to tissue separation to separate a tissue image, the separated tissue image is transformed into an image in the standard brain coordinate system, the resultant tissue image in the standard brain coordinate system is statistically compared with a pre-prepared tissue image of an able-bodied person to produce a brain tissue Z score map in the standard brain coordinate system, and the brain tissue Z score map is displayed together with the perfusion weighted Z score map in the standard brain coordinate system.

6. The medical image display processing method according to claim 5, wherein the perfusion weighted Z score map and the brain tissue Z score map in the standard brain coordinate system are transformed into images in an MRI coordinate system on the basis of the MRI morphological image and then displayed.

7. The medical image display processing method according to claim 3, wherein an MRI morphological image is inputted from the head of the subject using the MRI device, tissue is separated from the inputted MRI morphological image, separated tissue image is transformed into an image in the standard brain coordinate system, statistically compares the resultant tissue image in the standard brain coordinate system with a pre-prepared tissue image of the able-bodied person to produce a brain tissue Z score map in the standard brain coordinate system, and displays the brain tissue Z score map together with the perfusion weighted Z score map in the standard brain coordinate system, and when determining the transformation field for transforming the ASL-EPI image into an image in the standard brain coordinate system based on the ASL-EPI image, a transformation field from the coordinate system of the ASL-EPI image of the subject to a coordinate system of MRI morphological image of the same subject and a transformation field from the coordinate system of MRI morphological image of the subject to the coordinate system of the standard brain are determined respectively, and the transformation field from the coordinate system of the ASL-EPI image to the coordinate system of the standard brain is determined by combining the two transformation fields.

8. A medical image display processing method comprising the steps of:
inputting a functional image in an ASL coordinate system from a head of a subject by an ASL imaging method using an MRI device;
subjecting the inputted functional image to mask processing to extract only a region of cerebral parenchyma; and
displaying the resultant functional image containing only the extracted region of the cerebral parenchyma,
wherein the mask processing for extracting only the region of the cerebral parenchyma is performed using a mask image produced from an ASL-EPI image inputted simultaneously by the ASL imaging method,
determining transformation field from the ASL coordinate system to standard brain coordinate system based on the ASL-EPI image, and the functional image inputted by the ASL imaging method is transformed into an image in a standard brain coordinate system using the transformation field before the mask processing, and the resultant functional image of only the region of the cerebral parenchyma in the standard brain coordinate system is statistically compared with a pre-prepared functional image of only a region of cerebral parenchyma of an able-bodied person to produce and display a perfusion weighted Z score map in the standard brain coordinate system.

9. A medical image display processing device comprising:
image inputting means for inputting a functional image in an ASL coordinate system from a head of a subject by an ASL imaging method using an MRI device; and
image processing means for subjecting the inputted functional image to mask processing to extract only a region of cerebral parenchyma, wherein
the resultant functional image of only the extracted region of the cerebral parenchyma is displayed, and
wherein the image processing means performs the mask processing for extracting only the region of the cerebral parenchyma by using a mask image produced from an ASL-EPI image inputted simultaneously by the ASL imaging method,
and an MRI morphological image is inputted from the head of the subject using the MRI device, the image processing means determines transformation field from the ASL coordinate system of the subject to MRI coordinate system of the subject based on the inputted MRI morphological image and the ASL-EPI image, transforms the functional image of only the region of the cerebral parenchyma in the ASL coordinate system into an image in an MRI coordinate system using the transformation field, and the resultant functional image of the cerebral parenchyma is displayed to be overlaid on the MRI morphological image.

10. A medical image display processing device comprising:
- image inputting means for inputting a functional image in an ASL coordinate system from a head of a subject by an ASL imaging method using an MRI device; and
- image processing means for subjecting the inputted functional image to mask processing to extract only a region of cerebral parenchyma, wherein
- the resultant functional image of only the extracted region of the cerebral parenchyma is displayed, and
- wherein the image processing means performs the mask processing for extracting only the region of the cerebral parenchyma by using a mask image produced from an ASL-EPI image inputted simultaneously by the ASL imaging method, and further,
- the image processing means determines transformation field from the ASL coordinate system to standard brain coordinate system based on the ASL-EPI image, transforms the functional image inputted by the ASL imaging method into an image in a standard brain coordinate system after the mask processing using the transformation field, and then statistically compares the resultant functional image of only the region of the cerebral parenchyma in the standard brain coordinate system with a pre-prepared functional image of only a region of cerebral parenchyma of an able-bodied person to produce and display a perfusion weighted Z score map in the standard brain coordinate system.

11. The medical image display processing device according to claim 10, wherein the image processing means transforms the perfusion weighted Z score map in the standard brain coordinate system into an image in the ASL coordinate system by inverse transformation and then displays the resultant perfusion weighted Z score map.

12. The medical image display processing device according to claim 10, wherein an MRI morphological image is inputted from the head of the subject using the MRI device, and the image processing means performs tissue separation on the inputted MRI morphological image to separate a tissue image, transforms the separated tissue image into an image in the standard brain coordinate system, statistically compares the resultant tissue image in the standard brain coordinate system with a pre-prepared tissue image of the able-bodied person to produce a brain tissue Z score map in the standard brain coordinate system, and displays the brain tissue Z score map together with the perfusion weighted Z score map in the standard brain coordinate system.

13. The medical image display processing device according to claim 12 wherein the image processing means transforms the perfusion weighted Z score map and the brain tissue Z score map into an images in the standard brain coordinate system in an MRI coordinate system on the basis of the MRI morphological image and displays the resultant maps.

14. The medical image display processing device according to claim 10, wherein an MRI morphological image is inputted from the head of the subject using the MRI device, the image processing means conducts tissue separation from the inputted MRI morphological image, transforms the separated tissue image into an image in the standard brain coordinate system, statistically compares the resultant tissue image in the standard brain coordinate system with a pre-prepared tissue image of an able-bodied person to produce a brain tissue Z score map in the standard brain coordinate system, and displays the brain tissue Z score map together with the perfusion weighted Z score map in the standard brain coordinate system and,
- when determining the transformation field for transforming the ASL-EPI image into an image in the standard brain coordinate system based on the ASL-EPI image, determines a transformation field from the coordinate system of the ASL-EPI image of the subject to a coordinate system of MRI morphological image of the same subject and a transformation field from the coordinate system of MRI morphological image of the subject to the coordinate system of the standard brain respectively, and determines the transformation field for transforming the ASL-EPI image to an image in the coordinate system of the standard brain by combining the two transformation fields.

15. A medical image display processing device comprising:
- image inputting means for inputting a functional image in an ASL coordinate system from a head of a subject by an ASL imaging method using an MRI device; and
- image processing means for subjecting the inputted functional image to mask processing to extract only a region of cerebral parenchyma, wherein
- the resultant functional image of only the extracted region of the cerebral parenchyma is displayed, and wherein
- the image processing means performs the mask processing for extracting only the region of the cerebral parenchyma by using a mask image produced from an ASL-EPI image inputted simultaneously by the ASL imaging method, and further,
- the image processing means determines transformation field from the ASL coordinate system to standard brain coordinate system based on the ASL-EPI image, transforms the functional image inputted by the ASL imaging method into an image in a standard brain coordinate system before the mask processing using the transformation field, and then statistically compares the resultant functional image of only the region of the cerebral parenchyma in the standard brain coordinate system with a pre-prepared functional image of only a region of cerebral parenchyma of an able-bodied person to produce and display a perfusion weighted Z score map in the standard brain coordinate system.

* * * * *